US010132894B2

(12) United States Patent
Song et al.

(10) Patent No.: US 10,132,894 B2
(45) Date of Patent: Nov. 20, 2018

(54) MAGNETIC RESONANCE IMAGING METHODS

(71) Applicant: Schlumberger Technology Corporation, Sugar Land, TX (US)

(72) Inventors: Yi-Qiao Song, Newton Center, MA (US); Fei Han, New York City, NY (US); Jeffrey Paulsen, Brookline, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 1321 days.

(21) Appl. No.: 13/736,985

(22) Filed: Jan. 9, 2013

(65) Prior Publication Data

US 2013/0176026 A1 Jul. 11, 2013

Related U.S. Application Data

(60) Provisional application No. 61/585,507, filed on Jan. 11, 2012.

(51) Int. Cl.
*G01R 33/54* (2006.01)
*G01N 24/08* (2006.01)
*G01R 33/48* (2006.01)
*G01R 33/50* (2006.01)
*G01R 33/561* (2006.01)

(52) U.S. Cl.
CPC ........ *G01R 33/543* (2013.01); *G01N 24/081* (2013.01); *G01R 33/4824* (2013.01); *G01R 33/50* (2013.01); *G01R 33/5617* (2013.01)

(58) Field of Classification Search
CPC .. G01R 33/543; G01R 33/4824; G01R 33/50; G01R 33/5617; G01R 33/54; G01R 33/385; G01N 24/081; G01N 24/08
USPC .................................... 324/303, 307, 309
See application file for complete search history.

(56) References Cited

U.S. PATENT DOCUMENTS

| | | | | |
|---|---|---|---|---|
| 4,475,084 A | * | 10/1984 | Moore ................. | G01N 24/008 324/307 |
| 5,122,746 A | * | 6/1992 | King ..................... | G01R 33/44 324/300 |
| 5,363,041 A | | 11/1994 | Sezginer | |
| 5,378,865 A | | 1/1995 | Reneau | |

(Continued)

OTHER PUBLICATIONS

R.V. Mulkern, et al, "CPMG Imaging Sequences for High Field in Vivo Transverse Relaxation Stueis," Magnetic Resonance in Medicine, Academic Press, Duluth, MN, US, vol. 16, No. 1, Oct. 1, 1990, pp. 67-79 (#58024).

(Continued)

*Primary Examiner* — Rishi Patel (57) ABSTRACT

A method of investigating an object using nuclear magnetic resonance (NMR) equipment includes generating a one-dimensional projection of the object for each of a plurality of echoes utilizing echo train signal indications resulting from pulse sequences, and utilizing the plurality of one-dimensional projections, for each of the plurality of echoes, generating NMR image data for at least one location in the object. The NMR image data may be displayed. The displayed data may include a T2 decay curve, a T2 value display, a T2 distribution graph, or petrophysical data for at least one object location.

31 Claims, 6 Drawing Sheets

(56) References Cited

U.S. PATENT DOCUMENTS

| | | | | |
|---|---|---|---|---|
| 5,796,252 | A * | 8/1998 | Kleinberg | G01V 3/32 324/303 |
| 5,835,882 | A * | 11/1998 | Vienot | G01V 1/30 702/13 |
| 6,049,205 | A * | 4/2000 | Taicher | G01N 24/081 324/303 |
| 6,140,817 | A * | 10/2000 | Flaum | G01V 3/32 324/300 |
| 6,580,272 | B2 | 6/2003 | Freed et al. | |
| 7,343,192 | B2 * | 3/2008 | Reiderman | A61B 5/055 324/309 |
| 2004/0090230 | A1 * | 5/2004 | Appel | G01V 3/32 324/307 |
| 2007/0040553 | A1 * | 2/2007 | Hajimiri | G01R 33/446 324/309 |
| 2008/0150524 | A1 * | 6/2008 | Song | G01N 24/081 324/303 |
| 2009/0256562 | A1 * | 10/2009 | Gao | G01N 24/08 324/308 |
| 2010/0085052 | A1 * | 4/2010 | Johnson | G01R 33/4824 324/309 |
| 2011/0204892 | A1 * | 8/2011 | Li | G01N 24/081 324/309 |
| 2016/0275680 | A1 * | 9/2016 | Guo | G06T 5/002 |

OTHER PUBLICATIONS

F. Hennel, "Modification of the Carr-Purcell Sequence for Single-Shot Echo-Planar Imaging," Magnetic Resonance in Medicine, Academic Press, Duluth, MN, US, vol. 26, No. 1, Jul. 1, 1992 pp. 116-121. (#58025).

Extended search report for the equivalent European patent application No. 13151055.4 dated Aug. 26, 2013.

Lee, et al., "Multiplex RARE: a simultaneous multislice spin-echo sequence that fulfils CPMG conditions", Magnetic Resonance in Medicine, vol. 64, No. 1, Jul. 2010, pp. 299-305.

Müller, et al., "NMR imaging and volume-selective spectroscopy with a single surface coil", Journal of Magnetic Resonance, vol. 63, Issue 3, Jul. 1985, pp. 530-543.

Perlo, et al., "3D imaging with a single-sided sensor: an open tomograph", Journal of Magnetic Resonance, vol. 166, Issue 2, Feb. 2004, pp. 228-235.

Rooney, et al., "Application of the Extended Phase Graph Technique to Improve T2 Quantitation Across Sites", Proceedings of the International Society for Magnetic Resonance in Medicine, 19th Annual Meeting and Exhibition, Montreal, Quebec, vol. 19, Apr. 23, 2011, p. 138.

Extended European Search Report for EPO Application Serial No. 14160777.0 dated Jan. 22, 2015, 9 pages.

Nicholas J.S., et al.,"Accurate T2 NMR images," Med. Phys., vol. 10, No. 5, Sep. 1, 1983, pp. 642-645.

R. Mulkern, et al., "Spin-lock techniques and CPMG imaging sequences: A critical appraisal of T1p contrast at 0.15 T," Magnetic Resonance Imaging, Elsevier Science, Tarrytown, NY, US, vol. 7, No. 5, Sep. 1, 1989 pp. 437-444.

European Partial Search Report for the equivalent EP patent application No. 13151055.4 dated Apr. 13, 2013.

A. Timur, "Pulsed Nuclear Magnetic Resonance Studies of Porosity, Movable Fluid and Permeability of Sandstones", Journal of Petroleum Technology, Jun. 1979, p. 775.

M.D. Hurlimann, "Carr-Purcell Sequences with Composite Pulses", Journal of Magnetic Resonance, vol. 152, Issue 1, Sep. 2001, pp. 109-123.

T.W. Bornemana et al., "Application of optimal control to CPMG refocusing pulse design", Journal of Magnetic Resonance, vol. 207, Issue 2, Dec. 2010, pp. 220-223.

M. Hurlimann et al., Diffusion and Relaxation Effects in Generaly Stray Field NMR Experiments, Journal of Magnetic Resonance, vol. 148(2), pp. 367-378.

A. A. Khrapitchev, et al., "Centric-scan SPRITE magnetic resonance imaging with prepared magnetization," Journal of Magnetic Resonance, 2006, pp. 271-279.

A.V. Ouriadov, et al, "Thin film MRI—high resolution depth imaging with a local surface coil and spin echo SPI," Journal of Magnetic Resonance 169, No. 1 2004, pp. 174-186.

B.J. Balcom, et al, "Single-point magnetic resonance imaging (MRI) of cement based materials," Materials and Structures 36, 2003, pp. 166-182.

K.V. Romanenko, et al, "Permeability mapping in porous media by magnetization prepared centric-scan SPRITE," Experiments in Fluids 50, No. 2 2011, pp. 301-312.

D.J. Tyler, et al, "Magnetic resonance imaging with ultrashort TE (UTE) Pulse sequences: Technical considerations," Journal of Magnetic Resonance Imaging 25, No. 2 2007, pp. 279-289.

D. Idiyatullin, et al, "Fast and quiet MRI using a swept radiofrequency," Journal of Magnetic Resonance 181, No. 2, 2006, pp. 342-349.

G.R. Davies, et al, "Continuous-Wave magnetic Resonance Imaging of Short T2 materials," Journal of Magnetic Resonance, 2001, pp. 289-297.

L. Li, et al, "Quantitative discrimination of water and hydrocarbons in porous media by magnetization prepared centrio-scan SPRITE," Journal of Magnetic Resonance, 2007, pp. 282-292.

L. Li, et al, "Spin echo SPI methods for quantitative analysis of fluids in porous media," Journal of Magnetic Resonance 198, No. 2, 2009, pp. 252-260.

M.D. Robson, et al, "Clinical ultrashort echo time imaging of bone and other connective tissues," NMR in Biomedicine 19, No. 7 2006, pp. 765-780.

M. Halse, et al, "Centric scan SPRITE magnetic resonance imaging," Journal of Magnetic Resonance Imaging, 165, No. 2, 2003, pp. 219-229.

O.V. Petrov, et al, "T2 distribution mapping profiles with phase-encode MRI," Journal of Magnetic Resonance 209, No. 1 (2011), pp. 39-46.

S.D. Beyea, et al., "Imaging of Heterogeneous Materials with a Turbo Spin Echo Single-Point Imaging Technique," Journal of Magnetic Resonance 144, No. 2 2000, pp. 255-265.

* cited by examiner

MAGNETIC RESONANCE IMAGING METHODS

CROSS-REFERENCE TO RELATED APPLICATION

This application claims priority from U.S. Provisional Application 61/585,507, filed Jan. 11, 2012.

BACKGROUND

Field

This case relates to nuclear magnetic resonance (NMR) imaging methods. More particularly, this case relates to NMR imaging methods that provide, among other things, an ability to resolve short "T2" components. This case has applicability to the imaging of rocks, including rocks previously or presently bearing hydrocarbons, although it is not limited thereto.

Description of Related Art

Nuclear magnetic resonance (NMR) involves the application of a magnetic field to an object that impacts the magnetic moment (spin) of an atom in the object. In general, the magnetic field causes the atoms in the object to align along and oscillate (precess) about the axis of the applied magnetic field. The spin of the atoms can be measured. Of particular interest is the return to equilibrium of this magnetization; i.e., relaxation. For example, a state of non-equilibrium occurs after the magnetic field is released and the atoms begin to relax from their forced alignment. Longitudinal relaxation due to energy exchange between the spins of the atoms and the surrounding lattice (spin-lattice relaxation) is usually denoted by a time T1 when the longitudinal magnetization has returned to a predetermined percentage (i.e., 63%) of its final value. Longitudinal relaxation involves the component of the spin parallel or antiparallel to the direction of the magnetic field. Transverse relaxation that results from spins getting out of phase is usually denoted by time T2 when the transverse magnetization has lost a predetermined percentage (i.e., 63%) of its original value. The transverse relaxation involves the components of the spin oriented orthogonal to the axis of the applied magnetic field. The T2 measurement is often performed using a well-established Carr-Purcell-Meiboom-Gill (CPMG) pulse sequence which utilizes an initial 90 degree excitation pulse followed by a series of 180 degree (pi) refocusing pulses, and the data is typically analyzed using a Laplace inversion technique or an exponential curve fit.

NMR relaxation such as measured by T2 has been shown to be directly proportional to the surface-to-volume ratio of a porous material, $$1/T2 = \rho \cdot S/V_p \qquad (1)$$

where S is the total surface area of the material,
$V_p$ is the pore volume, and
$\rho$ is the surface relaxivity.
Surface relaxivity $\rho$ is a quantity (in micron/second) that defines the strength of the surface relaxation phenomenon. Because of this relationship, NMR is extensively used in petroleum exploration to obtain estimates of porosity, pore size, bound fluids, permeability, and other rock and fluid properties (i.e., "petrophysical data"). For example, it is known that the T2 distribution is closely related to the pore size distribution. Reservoir rocks often exhibit a wide range of T2 due to the difference in pore sizes, with observed T2s from several seconds down to tens of microseconds. Typically, signals at long T2 (e.g. >100 milliseconds) are from large pores and such fluids are considered to be producible. For shorter T2 signals, 3-50 milliseconds, the fluids are often considered to be bound by capillary force of the pores. For example, in sandstone rocks, signals at T2 below 30 ms are considered bound by capillary force and will not produce. Thus, a cutoff value, $T2_{cut}$, e.g., $T2_{cut}=30$ ms can be used to calculate the bound fluid volume $$BFV = \int_{T2min}^{T2cut} f(T2)dT2 \qquad (2)$$

where f(T2) is the T2 distribution, and
$T2_{min}$ is the minimum T2 obtained in the T2 distribution.
If f(T2) is the T2 distribution for the fully saturated sample, then the porosity Ø can be obtained by integrating f(T2) according to $$\emptyset = \int_{T2min}^{T2max} f(T2)dT2 \qquad (3)$$

where $T2_{max}$ is the maximum T2 exhibited in the sample. Signals with even shorter T2, such as T2<3 milliseconds, are often due to clay bound water or viscous (heavy) hydrocarbon. Some rocks contain a significant amount of kerogen that is solid organic matter and which may exhibit T2s down to tens of microseconds.

Conventional magnetic resonance imaging (MRI) techniques that work well for long T2 signals fail for short T2 signals. In particular, conventional methods such as the Multiple-Slice-Multiple-Echo (MSME) imaging technique use slice selection (discussed below), frequency encoding and phase encoding. Both frequency and phase encoding require that the gradient pulses be switched on and off between each of the adjacent refocusing pulses (pi pulses). Gradients for slice selection must also be turned on and off for each refocusing pulse as they will interfere with the frequency encoding pulses. Each switching procedure typically takes several hundred microseconds. As a result, the minimum echo time that can be achieved by the frequency encoding and phase encoding techniques is generally on the order of several milliseconds, preventing the resolution of shorter T2 values. "Lengthy" echo times (on the order of several milliseconds) also pose the problem that in order to obtain a sufficient signal to noise ratio (SNR) required to resolve each of the image elements (~1 mm³), relatively higher magnetic fields are necessary. However, with rock samples, at higher fields, a competing source of decay due to diffusion of the fluid and the induced magnetization of the rock will dominate and artificially shorten the apparent T2. The lengthy echo time of conventional MRI worsens the effect and further limits the samples appropriate for analysis.

Slice selection refers to the use of the differences in frequency response of the spins to a particular radio frequency (RF) pulse in the presence of an inhomogeneous magnetic field, and is a common component of MRI imaging. Typically, as in MSME, this is done to isolate a slice in the sample for imaging the sample with other image encoding techniques, i.e. phase encoding and frequency encoding. A gradient pulse will generate an approximately linear ramp in magnetic field strength that changes along a chosen direction in space. Because the frequency of the spins is proportional to field strength, the spin frequency will also form a linear ramp across the sample. As an RF pulse of finite duration and power will interact with spin of a limited range of frequencies, in the presence of a gradient this will interact with spins in a limited region of the sample and hence an MRI sequence will only image this portion of the sample. As the shape of the amplitude profile, the length, and frequency of the RF pulse will determine the exact nature of the response of spins at different frequencies and the amplitude and direction of the applied gradient can be controlled, the position and width of the slice can determined. Furthermore, the profile of excitation within the slice (as in Hadamard imaging) can also be controlled for further resolution as a function of slice depth. However, these techniques are combined with other image encoding methods (i.e. frequency encoding, phase encoding).

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to one aspect, a method is provided for performing NMR imaging on rocks that reliably provides indications of NMR properties, such as T2 distribution.

In another aspect methods are provided for conducting NMR imaging in a manner that permits resolving short T2 components (e.g., T2<3 milliseconds).

In one embodiment magnetic resonance imaging (MRI) of an object is conducted according to the following steps: (1) generating with NMR apparatus a field gradient along the object in a set direction, (2) obtaining a series of one-dimensional profiles (projections) of the object by subjecting the object under the field gradient to a series of RF pulse sequences, each sequence including an excitation pulse and refocusing pulses and recording the resulting echo train signals, each one-dimensional projection corresponding to a particular echo; (3) rotating the field gradient direction to different set directions while maintaining the magnitude of the field gradient, and repeating step (2) for each different direction, and obtaining one-dimensional projections for each echo for each field gradient direction; and (4) using the one-dimensional projections, obtaining an NMR image of the object or indications thereof for each of a plurality of echoes.

In one embodiment, the NMR images or indications thereof for one or more of the plurality of echoes is displayed.

In one embodiment, using the image or indications thereof for a plurality of echoes, T2 decay data is obtained for one or more locations in the object. The T2 decay data may be displayed as a number and/or as a plot. In another embodiment, T2 decay data is obtained for multiple locations of the object. The T2 decay data may be displayed as numbers and/or as plots.

In one embodiment, the T2 decay data is converted to a T2 distribution. The T2 distribution may be displayed in graphic form as a plot.

In one embodiment, at least one petrophysical information product dependent on the T2 decay data is obtained using the NMR image or indications thereof.

In one embodiment, the image of the object or indications thereof is obtained from the projections using an inverse Radon transformation.

In one embodiment, T2 decay data is converted to a T2 distribution using a Laplace inversion.

In one embodiment, the RF pulse sequence is a CPMG or a modified CPMG pulse sequence.

DETAILED DESCRIPTION

Figure 1:
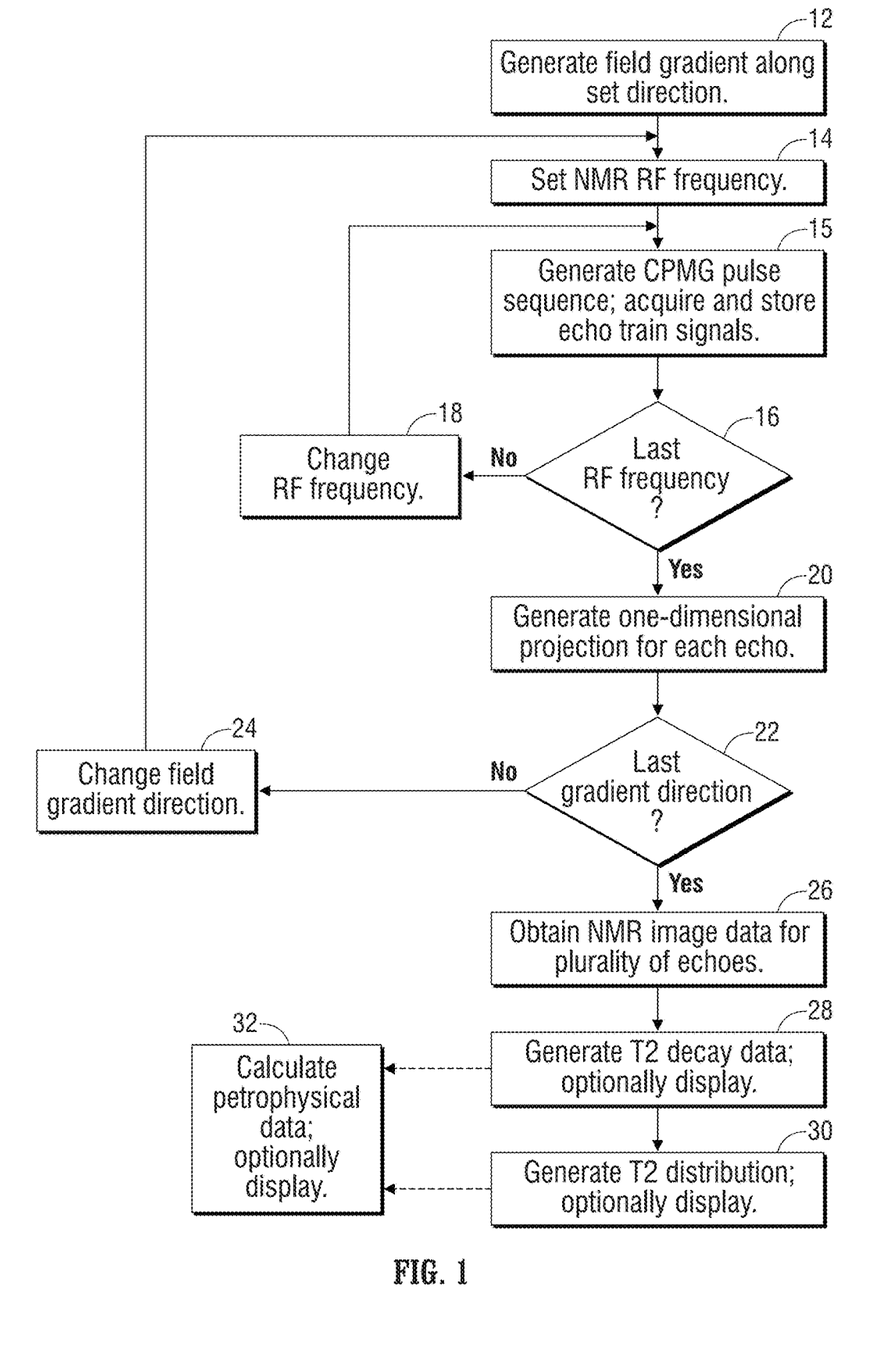
FIG. 1 is a flow diagram of one embodiment of a method.

A flow diagram of one embodiment of an imaging method is seen in FIG. 1. More particularly, an object is investigated using an NMR apparatus (not shown), where a field gradient Gxy( ) is generated by the NMR apparatus at 12 along a set (first) direction. At 14, the RF pulse frequency is set to a set (first) frequency. At 15, a CPMG pulse sequence is generated, and echo train signals are acquired and stored by the NMR apparatus as discussed below with reference to FIG. 2. At 16, a determination is made as to whether echo train signals have been acquired for a desired number of different RF frequencies. If not, the RF frequency is changed to a new set frequency at 18 thereby changing the object slice position as discussed below with reference to FIG. 3, and the method returns to 15 where a CPMG pulse sequence is generated with the new RF frequency and echo train signals are acquired and stored. Steps 15, 16, and 18 are repeated until a determination is made at 16 that signals resulting from CPMG pulse sequences at a sufficient number of RF frequencies have been recorded. Then at 20, using the echo train signals, a one-dimensional projection (profile) is generated for each echo as discussed below with reference to FIG. 3. At 22, a determination is made as to whether one-dimensional projections have been generated for a sufficient number of field gradient directions. If not, at 24, the gradient direction is changed (e.g., rotated) to a different set direction, and the method returns to step 14 et seq., to obtain additional one-dimensional projections. It will be appreciated that the direction may be changed not only in two dimensions (x-y space), but in three dimensions (x-y-z space) as desired. Regardless, when data for sufficient gradient directions have been obtained, the method continues at 26, where the one-dimensional projections are used to obtain an NMR image of the object or indications thereof (data) for each of a plurality of echoes. Images or indications of the object for one or more of the echoes are optionally displayed as discussed in more detail below with reference to FIGS. 6A-6D. In one embodiment, T2 NMR images are obtained using a transform such as a Radon transformation discussed in more detail below with reference to FIG. 4.

Figure 7A:
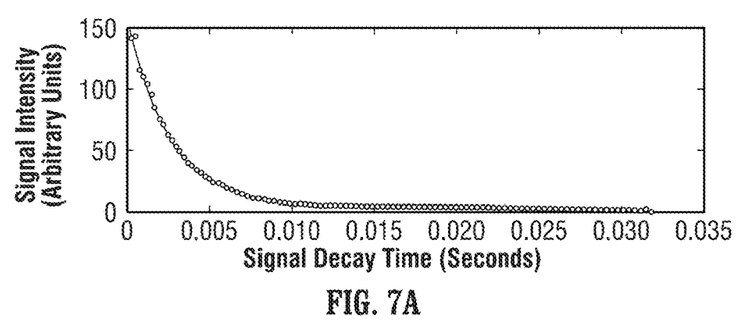
FIGS. 7A and 7B are plots of the T2 signal and the T2 distribution of a specific pixel of one of the copper sulfate doped tubes of water imaged in FIGS. 6A-6D.
Figure 7B:
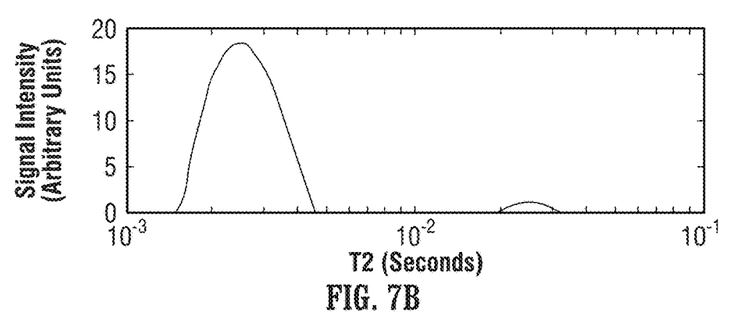
Figure 7C:
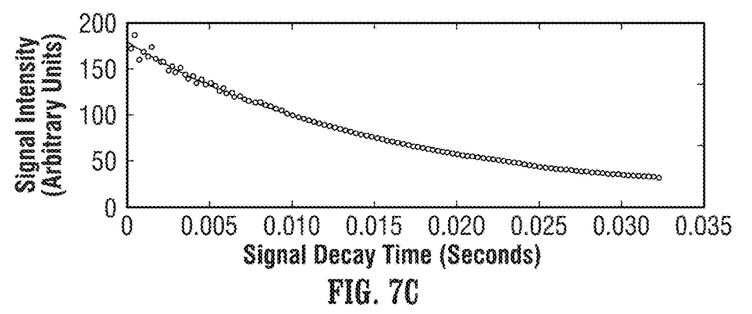
FIGS. 7C and 7D are plots of the T2 signal and the T2 distribution of a specific pixel of the second of the tubes of copper sulfate doped water imaged in FIGS. 6A-6D.
Figure 7D:
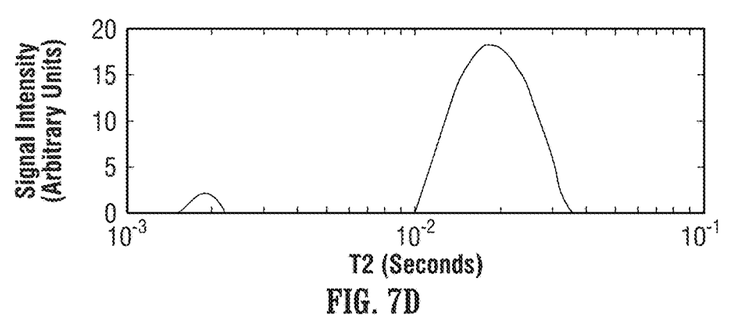

In one embodiment, at 28, T2 decay data is obtained for a location in the object using the image or indications thereof for a plurality of echoes. The T2 decay data is optionally displayed in the form of a number and/or as a plot as discussed in more detail below with reference to FIGS. 7A, 7C and 9A. In another embodiment, at 28, T2 decay data are obtained for multiple locations of the object and are optionally displayed in the form of a number and/or as a plot.

In one embodiment, at 30, the T2 decay data for one location in the object are processed, e.g., using a Laplace inversion to generate a T2 distribution. The T2 distribution may be displayed in graphic form. Additionally or alternatively, a T2 value may be obtained from the T2 distribution data. In another embodiment, at 30, T2 decay data for multiple locations in the object are converted to a plurality of T2 distributions and are optionally displayed as discussed in more detail below with reference to FIGS. 7B, 7C and 9B.

In one embodiment, the T2 decay data and/or distributions obtained at 28 and/or 30 are used at 32 to generate indications of rock parameters (attributes). By way of example and not limitation, as described in U.S. Pat. No. 5,387,865, which is incorporated by reference herein in its entirety, the fluid flow permeability of the porous object (rock) under study may be determined using inter alia a T2 value determination. The fluid flow permeability may be displayed. As another example, as described in U.S. Pat. No. 5,363,041, which is incorporated by reference herein in its entirety, unbound fluid volume (and bound fluid volume) of the object (formation) under study may be determined using inter alia a T2 determination. The unbound fluid volume and/or bound fluid volume may be displayed. As disclosed in A. Timur, "Pulsed Nuclear Magnetic Resonance Studies of Porosity, Movable Fluid and Permeability of Sandstones", *Journal of Petroleum Technology*, June 1979, p. 775, indications of T2 may be used in making determinations of porosity, permeability, and movable fluid of sandstones which may be displayed.

While FIG. 1 provides one embodiment in steps 14-20 for generating one-dimensional projections (profiles) for a desired number of echoes, it should be appreciated that the one-dimensional projections can be obtained in other manners. By way of example and not by way of limitation, instead of repeatedly changing the RF frequency and acquiring resulting echo train signals in order to generate the one-dimensional projections, the position of the sample can be varied (e.g., slid) so that different slices of the sample are investigated without changing the RF frequency. By way of another example, and not by way of limitation, instead of changing the RF frequency and acquiring echo train signals, an offset pulse B0 may be applied on top of the gradient so that the same RF frequency can correspond to a different position. Thus, by applying different offset pulses B0, B1 . . . , different slices of the sample are investigated without changing the RF frequency. Other methods and mechanisms can be used as well, provided that one-dimensional projections are generated for the desired number of echoes while avoiding gradient switching during the CPMG pulse sequencing.

As previously mentioned, one embodiment entails conducting CPMG pulse sequences under a field gradient Gxy( ) and acquiring echo signals. While the CPMG pulse sequence refers to a specific sequence (described in more detail below with reference to FIG. 2), other "improved" pulse sequences that will generate an appropriate echo train may be utilized. Thus, by way of example and not by way of limitation, a modified CPMG as described in M. D. Hurlimann, "Can-Purcell Sequences with Composite Pulses", *Journal of Magnetic Resonance*, Vol. 152, Issue 1, September 2001, pp. 109-123, may be utilized. Also, by way of example and not by way of limitation, U.S. Pat. No. 6,580,272, which is incorporated by reference herein in its entirety, discloses a split-180 signal in order to detect a steady state free precession signal. Another example is described in T. W. Bornemana et al., "Pulses Derived from Optimal Control Theory", *Journal of Magnetic Resonance*, Vol. 207, Issue 2, December 2010, pp. 220-223. Other pulse sequences can be used as well such as complex (shaped) RF pulses or composite pulses, provided that they are slice selective or their frequency profiles can be used to invert for one-dimensional projections for a desired number of echoes.

Figure 2:
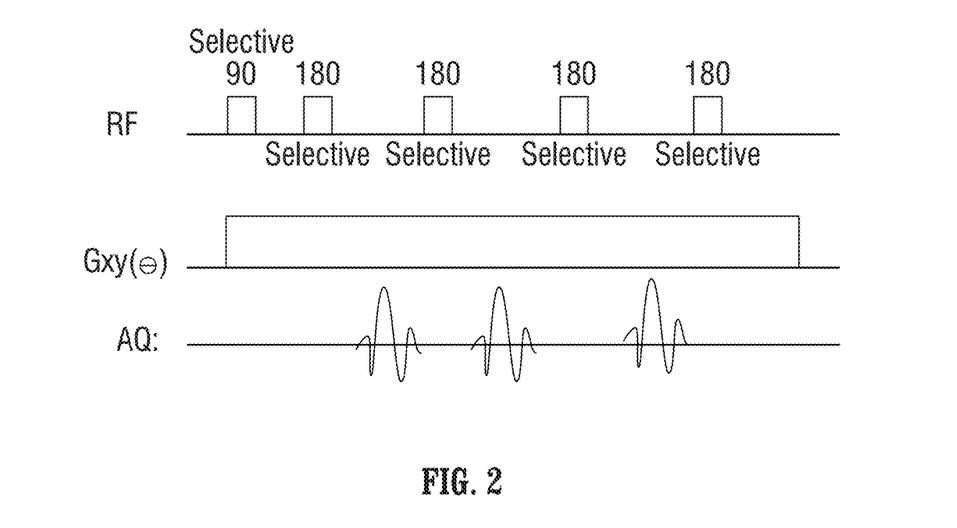
FIG. 2 is a time diagram displaying indications of RF pulses, a gradient, and an acquired echo train useful in the method of FIG. 1.

Turning now to FIG. 2, a standard CPMG pulse sequence is seen with an initial 90 degree frequency-selective (excitation) pulse followed by a series of frequency-selective 180 degree (refocusing) pulses. As seen in FIG. 2, the field gradient Gxy( ) is maintained constant during the CPMG pulse sequence. Also, as seen in FIG. 2, following each selective refocusing pulse, an echo signal AQ is acquired. It will be appreciated that the CPMG pulse sequence may utilize tens, hundreds, or thousands of refocusing pulses, and therefore tens, hundreds, or thousands of echo signals can be acquired by the NMR equipment.

Figure 3:
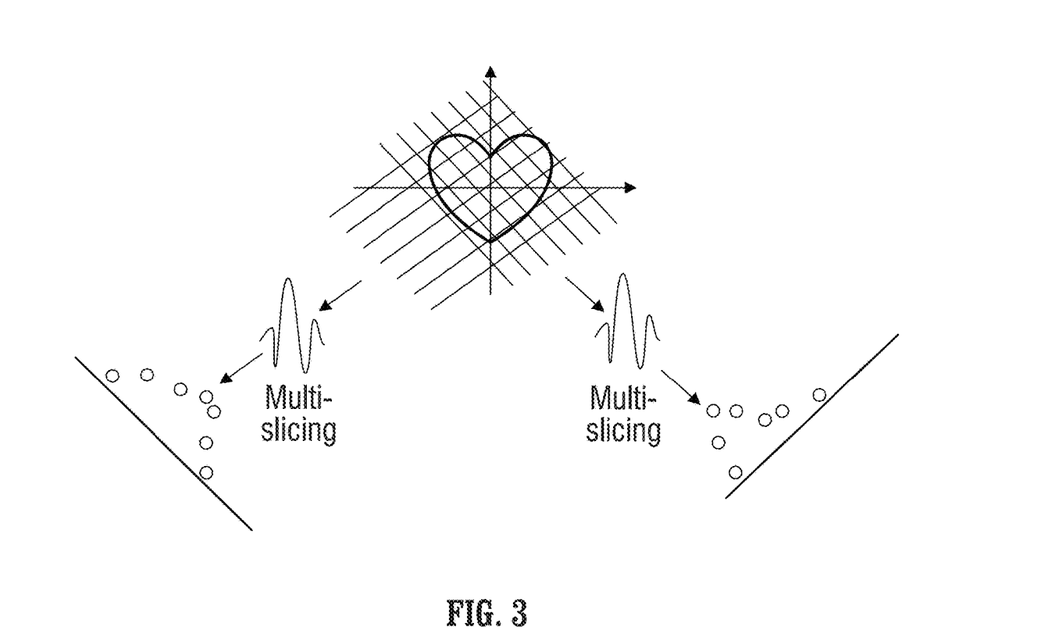
FIG. 3 is a diagram helpful in understanding slicing in multiple projections.

For any given field gradient direction, changing the RF frequency changes the slice (as seen in FIG. 3) of the object being investigated, and this may be done at desired granularity. Thus, while six slices are shown in FIG. 3, it will be appreciated that a different number of slices may be generated. Similarly, for a particular echo, the number of one-dimensional projections generated depends on the number of times the gradient direction was changed (e.g., rotated) at step 24 of FIG. 1. Thus, while only two one-dimensional projections are seen in FIG. 3 at ninety degree angles relative to each other, it will be appreciated that many more projections may be generated by changing the field gradient direction with more granularity. It will be appreciated that in order to change the field gradient, the sample may be rotated, or the NMR equipment may be moved or adapted to generate field gradients of different directions.

According to one aspect, and as previously suggested, the CPMG sequence utilized can be tailored as desired for the context of the object investigation. For example, for imaging of hydrocarbon-bearing rock, specific dynamics known with respect of NMR logging as discussed by M. Hurlimann et al., "Diffusion and Relaxation Effects in Generaly Stray Field NMR Experiments, *Journal of Magnetic Resonance*, Vol. 148(2), pp. 367-378, may be applicable. Likewise, modifications to improve the CPMG, (e.g., improving the echo refocusing, controlling the bandwidth, minimizing interference between different slices, diffusion editing to provide additional information on diffusion, and saturation recovery for T1 information, as is done in wireline and LWD NMR logging) may be utilized.

As previously mentioned, data points are derived from echoes. A single intensity value is extracted from each echo to get the value of the projection. In one embodiment, the value of the data point is taken from the intensity of the echo at the center of the echo signal AQ. In another embodiment, a maximum value may be taken. In yet another embodiment, the echo is acquired with the same frequency as the CPMG pulse, and any of many techniques may be used to extract echo intensities such as, by way of example and not by way of limitation, integrating over a range of frequencies, or using a matched filter. It will be appreciated that depending upon the details of CPMG pulse sequence utilized, different sensitivities may result across the slice's profile (for example a square pulse will have a slice profile similar to a sinc function, a Gaussian pulse a Gaussian profile). In one embodiment, knowledge of the slice profile and the use of overlapping slices in combination with deconvolution can be used to enhance the resolution of any set of projections beyond the natural slice width.

Figure 4:
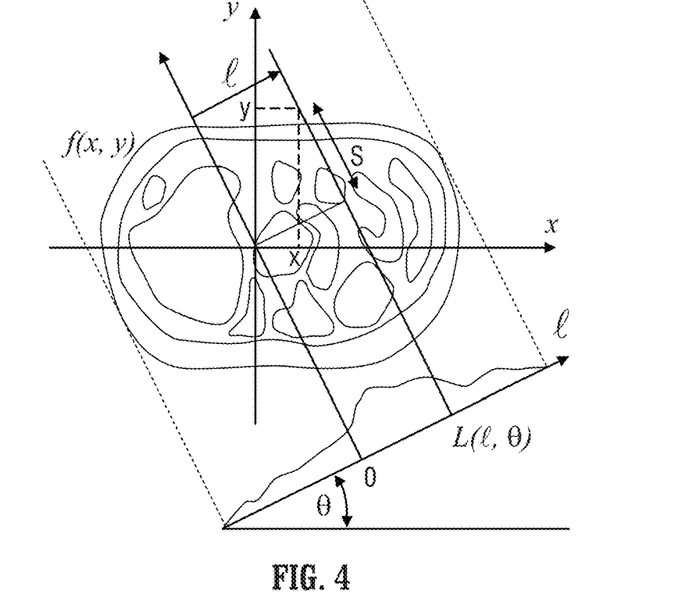
FIG. 4 is a diagram illustrating a two-dimensional Radon transform as line integrals.

As previously mentioned, one-dimensional projections are used to obtain an NMR image of the object or indications thereof (data values for each point or pixel of interest) for each of a plurality of echoes. In one embodiment, the images are obtained using a transform such as a Radon transformation which is the mathematical basis for tomographic imaging from projections. The two-dimensional Radon transform set forth in Equation (4) below is simply a line integral, as shown in FIG. 4, $$g(l, \theta) = \int_{-\infty}^{\infty}\int_{-\infty}^{\infty} f(x, y)\delta(x\cos\theta + y\sin\theta - l)dxdy \quad (4)$$

where is the gradient direction (angle) of the signal, and l is the slice position set by the RF frequency, and is a Dirac delta.

Figure 5:
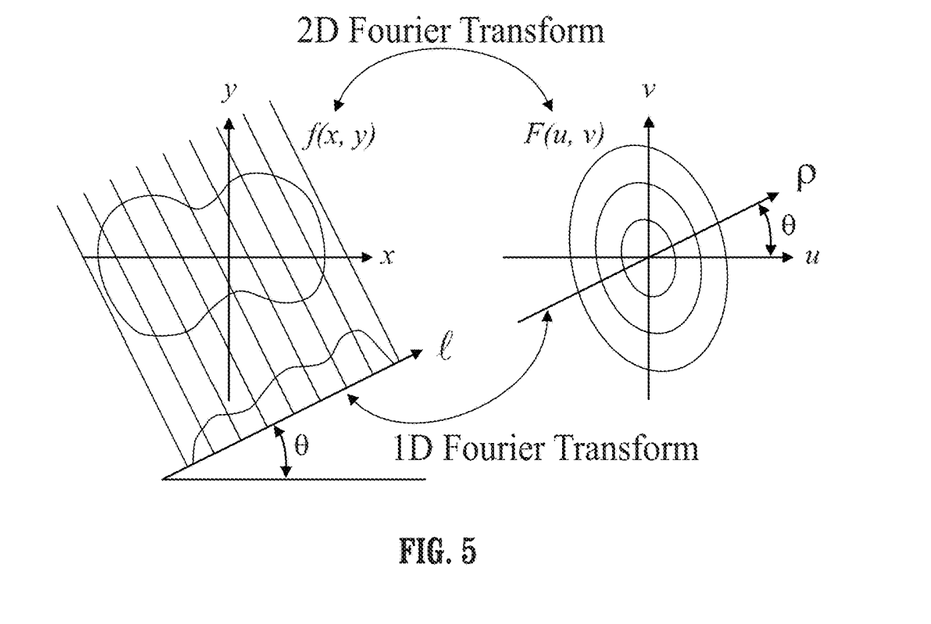
FIG. 5 is a diagram useful in understanding the Projection-Slice Theorem.
Figure 6A:
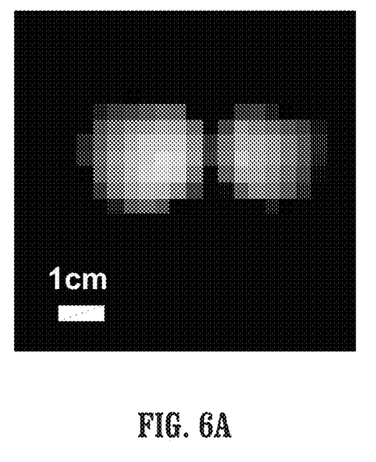
FIGS. 6A-6D are magnetic resonance images generated for four different echoes using the method of FIG. 1 showing two tubes of water doped with different amounts of copper sulfate.
Figure 6B:
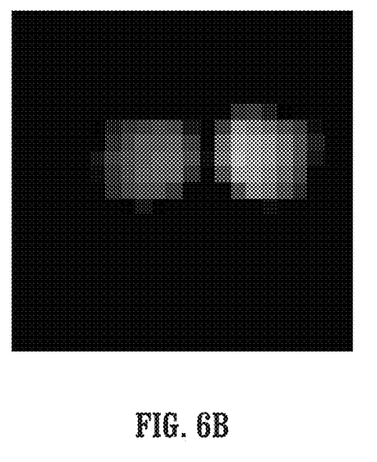
Figure 6C:
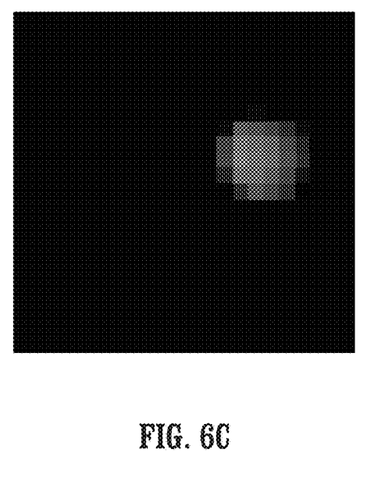
Figure 6D:
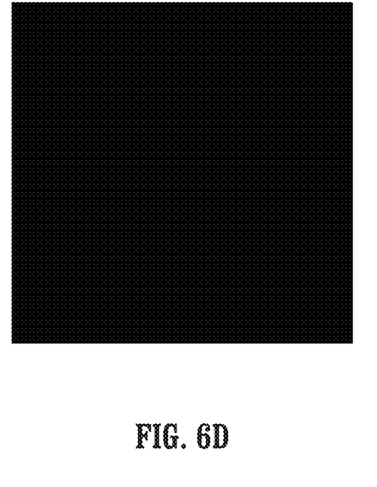

The Radon transform is closely related to the Fourier transform by the Projection-Slice Theorem which is the basis for image reconstruction algorithms. The Projection-Slice Theorem simply states, as seen in FIG. 5, that the one-dimensional (1D) Fourier transform of the projection equals the two-dimensional (2D) Fourier transform along the radial line at that angle ( ). According to the Projection-Slice Theorem, to reconstruct the image, an inverse of the 2D Fourier transform can be taken in polar coordinates which is known as a filtered back-projection or inverse Radon transform. The inverse 2D Fourier transform in Cartesian coordinates can be represented by:

$$f(x, y) = \iint F(u, v)e^{j2\pi(xu+yv)} dudv \quad (5)$$

The transform is implemented in most mathematics software packages, for instance MATLAB® (a trademark of MathWorks, Inc. of Natick, Mass., USA), as a 'fast' algorithm that computes the same result as the integral form. The inverse 2D Fourier transform in polar coordinates can be represented as:

$$f(r, \theta) = \quad (6)$$

$$\sum_{n=-\infty\to\infty} (j)^n e^{jn\theta} 2\pi \int_{0\to\infty} \rho \left[\frac{1}{2\pi}\int_{-\pi\to\pi} G(\rho, \phi)e^{-jn\phi}d\phi\right] J_n(2\pi\rho r)d\rho$$

where ρ is the Fourier conjugate variable to l and G (p, φ) is the 1D Fourier transform of the 1D projection data collected for each gradient angle φ. It is noted that multiple 'fast' algorithms exist to solve the discrete form of this equation without directly computing the integrals and are implemented in common mathematics software suites such as MATLAB®.

Once the image of each echo time is reconstructed, e.g., using inverse Radon transformations, the individual image elements (pixels) or averages over regions of the image may be used to construct individual T2 decay curves. For example, and as discussed in more detail below with reference to FIGS. 6A-6D and 7A-7D, with the reconstructions, values are obtained for each echo for each point or pixel in the image. The value for each pixel may then be plotted as a function of (echo) time to provide a T2 decay curve. The curve for each pixel may then be analyzed by any number of the existing analysis techniques for CPMG data such as exponential or stretched exponential curve fitting, or inverse Laplace transformation, to generate "answer products" such as T2 distributions. For CPMG analysis techniques that are equivalent to taking a linear transform for the CPMG decay, this analysis step may be done before the inverse Radon transform (or equivalent image reconstruction technique) and instead of the image reconstruction for the individual echoes, and the same image reconstruction technique may be applied directly to values extracted from the CPMG decays.

Turning now to FIGS. 6A-6D, four reconstructed images are shown resulting from an NMR investigation of two tubes of water doped with different amounts of copper sulfate at different echo times (e.g., the first, eighth, thirty-second, and one hundred twenty-eighth echoes). The images were obtained and reconstructed using the imaging method described above with respect to FIG. 1. The intensities of particular pixels were then plotted as a function of time. For example, the intensities (magnitudes) of the echoes for pixel 10×7 which appears located at the center of the left tube of doped water were plotted in FIG. 7A. The resulting curve of FIG. 7A was then analyzed using an inverse Laplace transform to generate the T2 distribution shown in FIG. 7B. As will be appreciated, FIG. 7B indicates that the T2 decay for that pixel is centered about 2.5 milliseconds which is a very short T2 time. Similarly, the intensities of the echoes for pixel 10×15 which appears located at the center of the right tube of doped water were plotted in FIG. 7C. The resulting curve of FIG. 7C was then analyzed to generate the T2 distribution shown in FIG. 7D. As will be appreciated, FIG. 7D indicates that the T2 decay for that pixel is centered about 19 milliseconds which is a short T2 time.

Figure 8:
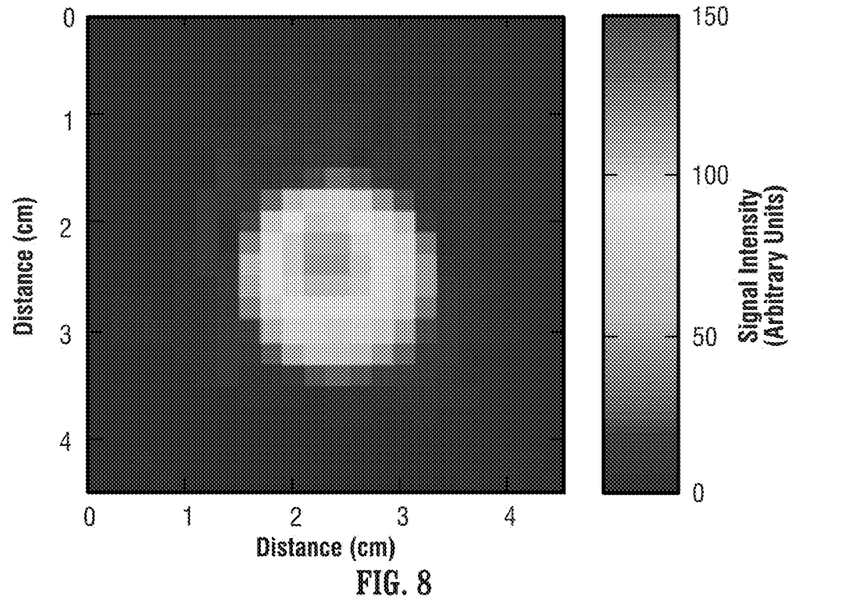
FIG. 8 is a magnetic resonance image generated using the method of FIG. 1 of a shale sample.
Figure 9A:
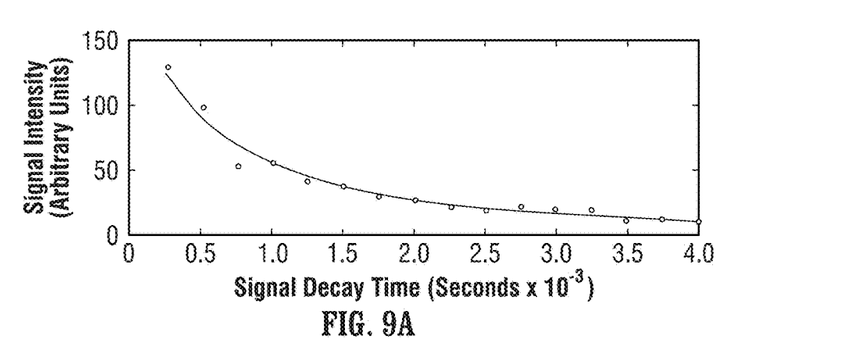
FIGS. 9A and 9B are plots of the T2 signal and the T2 distribution of a specific pixel of the image of FIG. 8.
Figure 9B:
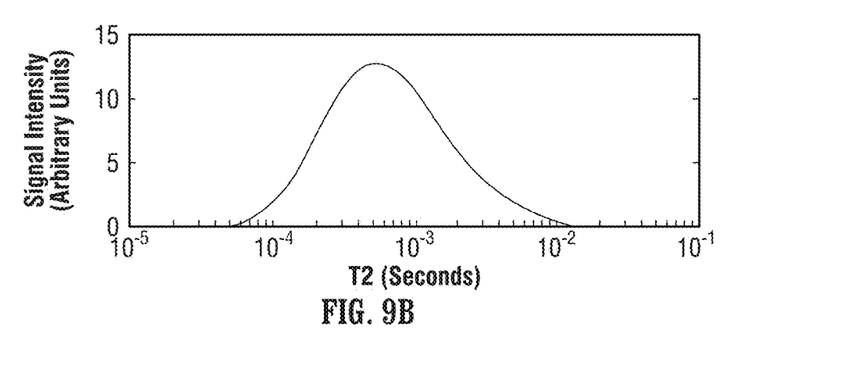

A shale sample was subjected to the NMR pulse sequence and image reconstruction discussed above with reference to FIG. 1. The resulting first echo image for a particular pixel (pixel 11×11) is seen in FIG. 8. Using the image reconstructions for sixteen echoes, the T2 decay curve for pixel 11×11 was generated as seen in FIG. 9A. The curve of FIG. 9A was then analyzed to generate the T2 distribution shown in FIG. 9B. As will be appreciated, FIG. 9B indicates that the T2 decay for that pixel is centered at approximately 500 microseconds, a very short T2 time that may be indicative of viscous oil, bitumen, and/or kerogen.

It should be appreciated that using the NMR pulse sequence and image reconstruction techniques discussed above, various valuable answer products may be obtained. For example, T2 decay curves may be obtained as shown and described with respect to FIGS. 7A, 7C, and 9A. Alternatively, or in addition, T2 distribution curves may be obtained as shown and described with respect to FIGS. 7B, 7D, and 9B. Alternatively, or in addition, T2 values (times) may be obtained as described with reference to the center of each of the distribution curves of FIGS. 7B, 7D, and 9B. The T2 values may be shown as numerical answer products, or on graphs or plots. By way of example and not limitation, the T2 values for different pixels may be represented as numbers for each pixel on a chart or on a plot, or as different colors or intensities with an appropriate key on a chart or on a plot. Alternatively, or in addition, petrophysical data such as determinations of permeability (estimates), porosity, or bound or unbound water, and/or the heterogeneity of any of these properties, may be determined using the T2 information obtained, and may be displayed numerically, on graphs or plots, or otherwise.

There have been described and illustrated herein several embodiments of investigating objects using NMR measurements. While particular embodiments have been described, it is not intended that the embodiments limit the scope hereof. Thus, many changes may be made. For example, while the gradient was described with respect to FIG. 2 as being constantly on, the gradient may be temporarily turned off in order to reduce duty cycle for the gradient amplifier. This may be done between CPMG trains. Also, the inverse Radon transform may be accomplished by different algorithms, and while filtered back-projection was described, other reconstruction techniques such as compressed sensing may be used to similar effect. Further, while a particular sequence of steps was described with respect to FIG. 1 where one-dimensional projections are generated for the echoes prior to changing the field gradient direction, it will be appreciated that the sequence of steps is not limiting and may be changed. For example, all echo data may be stored for all gradient directions prior to generating the one-dimensional projections. In addition, while the embodiments were described as generating particular "answer products", it will be appreciated that other answer products could be generated and displayed. It will therefore be appreciated by those skilled in the art that yet other modifications could be made. Accordingly, all such modifications are intended to be included within the scope of this disclosure as defined in the following claims. In the claims, means-plus-function clauses, if any, are intended to cover the structures described herein as performing the recited function and not only structural equivalents, but also equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method of investigating an object using nuclear magnetic resonance (NMR) equipment, comprising the steps of:
   a) generating a constant-magnitude field gradient along a set direction;
   b) obtaining a series of one-dimensional profiles of the object by subjecting the object under the constant-magnitude field gradient to a series of RF pulse sequences, each RF pulse sequence generating a series of echoes and recording echo train signals resulting from the series of RF pulse sequences interacting with the object, each one-dimensional profile corresponding to a particular echo time;
   c) changing the set direction of the field gradient to different set directions while maintaining the magnitude of the constant-magnitude field gradient, and repeating step b) for each different set direction of the field gradient, thereby obtaining one-dimensional projections for each echo time for each set direction of the field gradient; and
   d) using the projections, generating two- or three-dimensional NMR image data for each of a plurality of echo times for at least one location in the object.

2. A method according to claim 1, wherein the series of RF pulse sequences is generated by (1) setting the RF frequency to a set frequency, (2) generating an NMR pulse sequence with the RF frequency at the set frequency, (3) changing the RF frequency to a new set frequency and repeating step (2), and (4) repeating step (3) a number of times.

3. A method according to claim 1, wherein the series of RF pulse sequences is generated by (1) setting the RF frequency to a set frequency, (2) generating an NMR pulse sequence with the RF frequency at the set frequency, (3) moving the object and repeating step (2), and (4) repeating step (3) a number of times so that different slices of the object are investigated without changing the RF frequency.

4. A method according to claim 1, wherein the series of RF pulse sequences is generated by (1) setting the RF frequency to a set frequency, (2) generating an NMR pulse sequence with the RF frequency; (3) applying an offset pulse BO on top of the field gradient, (4) repeating steps (2) and (3) a number of times while changing a value of the offset pulse so that different slices of the object are investigated without changing the RF frequency.

5. A method according to claim 1, further comprising using the NMR image data for each of the plurality of echo times, generating T2 decay curve data for the at least one location in the object.

6. A method according to claim 5, further comprising using the T2 decay curve data, generating a T2 decay curve display for the at least one location in the object.

7. A method according to claim 5, further comprising using the T2 decay curve data, generating T2 distribution data for the at least one location in the object.

8. A method according to claim 7, further comprising using the T2 distribution data, generating a display relating to the T2 distribution data.

9. A method according to claim 8, wherein the display is a T2 distribution graph.

10. A method according to claim 8, wherein the display is a display of a T2 value.

11. A method according to claim 5, further comprising using the T2 decay curve data, generating an indication of petrophysical data for the at least one location in the object.

12. A method according to claim 11, further comprising generating a display relating to the indication of petrophysical data.

13. A method according to claim 1, wherein the generating NMR image data comprises utilizing an inverse Radon transformation.

14. A method according to claim 1, wherein the object is a rock from a hydrocarbon -bearing formation.

15. A method according to claim 14, wherein the rock has a location having a T2 of less than 3 milliseconds.

16. A method according to claim 2, wherein the NMR pulse sequence is a CPMG pulse sequence.

17. A method according to claim 16, wherein the NMR CPMG pulse sequence includes a plurality of frequency-selective 180 degree refocusing pulses.

18. A method according to claim 16, wherein said constant-magnitude field gradient is turned off between CPMG trains.

19. A method of investigating a hydrocarbon-bearing rock using nuclear magnetic resonance (NMR) equipment, comprising the steps of:
   a) with a constant-magnitude field gradient set along a first direction, sequentially setting the NMR RF pulse frequency to a plurality of different frequencies, and at each different frequency generating an NMR pulse sequence with an excitation pulse and refocusing pulses and acquiring and storing indications of echo train signals resulting from the NMR pulse sequence interaction with the rock;

b) changing the direction of the constant-magnitude field gradient a plurality of times, and repeating step a) for each field direction;

c) utilizing the indication of echo train signals, generating a plurality of one-dimensional projections of the rock, each of said plurality of one dimensional projections corresponding to one of a plurality of echo times of said echo train signals;

d) utilizing the plurality of one-dimensional projections, for each of the plurality of echo times, generating two- or three-dimensional NMR image data for at least one location in the rock; and e) displaying the NMR image data.

20. A method according to claim 19, wherein the NMR image data comprises at least one of a T2 decay curve display, a T2 distribution graph, a T2 value display, and petrophysical data for the at least one location in the rock.

21. A method according to claim 20, wherein the generating NMR image data comprises utilizing an inverse Radon transformation.

22. A method according to claim 19, wherein the NMR pulse sequence is a CPMG pulse sequence.

23. A method according to claim 20, wherein the rock has a location having a T2 of less than 3 milliseconds.

24. A method according to claim 22, wherein said constant-magnitude field gradient is turned off between CPMG trains.

25. A method of investigating an object using nuclear magnetic resonance (NMR) equipment, comprising the steps of:

a) generating a constant-magnitude field gradient along a set direction;

b) setting an RF pulse frequency to a set frequency;

c) generating an NMR CPMG pulse sequence with the constant-magnitude field gradient at the set direction and the RF pulse frequency at the set frequency;

d) acquiring and storing indications of echo train signals as a result of the NMR CPMG pulse sequence interaction with the object;

e) changing the RF pulse frequency to a new set frequency and repeating steps c) and d) at the newly set frequency;

f) repeating step e) a plurality of times;

g) changing the set direction of the constant-magnitude field gradient to a new set direction and repeating steps b) through f) at the newly set direction;

h) repeating step g) a plurality of times;

i) for each new set direction of the field gradient, generating respective one-dimensional projections of the object for each of a respective plurality of echo times utilizing the indications of echo train signals acquired as a result of the NMR CPMG pulse sequence interaction with the object at multiple NMR RF pulse frequencies, thereby obtaining a plurality of one-dimensional projections;

j) from the plurality of one-dimensional projections, for each of the plurality of echo times, generating two- or three-dimensional NMR image data for at least one location in the object.

26. A method according to claim 25, further comprising:

k) displaying the NMR image data.

27. A method according to claim 26, wherein the NMR image data comprises at least one of a T2 decay curve display, a T2 distribution graph, a T2 value display, and petrophysical data for the at least one location in the object.

28. A method according to claim 25, wherein the generating NMR image data comprises utilizing an inverse Radon transformation.

29. A method according to claim 25, wherein the object is a rock from a hydrocarbon-bearing formation.

30. A method according to claim 29, wherein the rock has a location having a T2 of less than 3 milliseconds.

31. A method according to claim 25, wherein said constant-magnitude field gradient is turned off between CPMG trains.

* * * * *